United States Patent
Sankaranarayanan

(12) 
(10) Patent No.: US 6,281,246 B2
(45) Date of Patent: Aug. 28, 2001

(54) PHARMACEUTICAL COMPOSITION WITH SOTALOL COMBINATION AND THEIR USE IN TREATMENT OF CARDIAC AILMENTS

(75) Inventor: Alangudi Sankaranarayanan, Ahmedabad (IN)

(73) Assignee: Torrent Pharmaceutical Ltd., Gujarat (IN)

( * ) Notice: Subject to any disclaimer, the term of this patent is extended or adjusted under 35 U.S.C. 154(b) by 0 days.

(21) Appl. No.: 09/739,276

(22) Filed: Dec. 19, 2000

Related U.S. Application Data

(63) Continuation-in-part of application No. PCT/IB99/00322, filed on Feb. 22, 1999.

(30) Foreign Application Priority Data

Feb. 5, 1999 (IN) ................................................ 89/CAL/99

(51) Int. Cl.⁷ .................................................... A61K 31/18
(52) U.S. Cl. .............................................................. 514/605
(58) Field of Search ............................................. 514/605

(56) References Cited

U.S. PATENT DOCUMENTS 5,089,526  2/1992  Simon et al. ........................ 514/605

FOREIGN PATENT DOCUMENTS

2286529 A  8/1995  (GB) .............................. A61K/31/18

OTHER PUBLICATIONS

C Funck—Brentano, European Heart Journal (1993) 14 (Supplement 11) 30–35.

Cardiac Arrhythmia Suppression Trial (CAST) Investigators (New Engl J Med. 1989; 321:407–412).

Cardiac Arrhythmia Suppression Trial II (CAST II) Investigators (New Engl J Med. 1992; 327; 227–233).

Coplen et al (Circulation 1990 Oct; 82(4) : 1106–16).

The Cardiac Arrest in Seattle : Conventional Versus Amiodarone Drug Evaluation (CASCADE) Study (Am J Cardiol 1993; 72: 280–287).

Jay W Mason for The Electrophysiologic Study Versus Electrocardiographic Monitoring (ESVEM) Investigators (New Engl J Med. 1993; 329 : 452–8).

Callaghan et al (Am J Cardiol, 1996; 78: (4A) (54–60)).

The Survival With Oral d—Sotalol (SWORD) trial (Am J Cardiol 1995; 75: 1023–27).

International Search Report for PCT/IB99/00322 (Jul. 1999).

Database WPI, Section Ch, Week 8932, Derwent Publications Ltd., London, GB; Class B05, AN 89–230857, XP002109599 & JP 01 165569 A (Mitsui Toatsu Chem Inc), Jun. 29, 1989.

International Preliminary Examination Report for PCT/IB99/00322 dated Feb. 27, 2001.

*Primary Examiner*—Raymond Henley, III
(74) *Attorney, Agent, or Firm*—Sughrue, Mion, Zinn, Macpeak & Seas, PLLC

(57) ABSTRACT

The invention discloses a safer Antiarrhythmic drug with controlled Beta Adrenergic activity which comprises a combination of dextro- and laevo-rotatory isomers of sotalol as active ingredients, pharmaceutical compositions with said combination as active ingredients and its preparation and use of the said combination in the treatment of cardiac ailments in mammals including human beings.

15 Claims, No Drawings

PHARMACEUTICAL COMPOSITION WITH SOTALOL COMBINATION AND THEIR USE IN TREATMENT OF CARDIAC AILMENTS

This application is a continuation-in-part of International Application Ser. No. PCT/IB99/00322 filed Feb. 22, 1999, the disclosure of which is incorporated herein by reference, which international application was published by the International Bureau in English on Aug. 10, 2000.

BACKGROUND OF THE INVENTION

1. Field of the Invention

The invention relates to an antiarrhythmic drug and particularly to a combination of d- and l-isomers of sotalol, being N-[4-[1-hydroxy-2-[(1-methylethyl)amino]ethyl] phenyl] methane sulfonamide, as a safer class III antiarrhythmic drug with reduced beta adrenergic blockade.

2. Description of the Related Art

Drug treatment of cardiac arrhythmias has undergone rapid changes during the last decade. Experimental studies have shown that drugs that act by delaying conduction, though are able to suppress ventricular arrhythmias, also increase the mortality particularly in patients with cardiac disease.

Cardiac Arrhythmia Suppression Trial (CAST) Investigators (New Engl J Med 1989; 321:407–412) and Cardiac Arrhythmia Suppression Trial II (CAST II) Investigators (New Engl J Med 1992; 327:227–33) have shown that drugs like flecainide, encainide and moricizine which act by blocking sodium channels cause increased mortality in patients who survived from acute myocardial infarction despite markedly suppressing premature ventricular contractions.

Coplen et al (Circulation 1990 Oct. 82(4):1106–16) have shown that even drugs like quinidine which has been used for so long in antiarrhythmic therapy increase the mortality in a variety of settings.

The Cardiac Arrest in Seattle: Conventional Versus Amiodarone Drug Evaluation (CASCADE) study (Am J Cardiol 1993; 72:280–287) have further shown that, amiodarone, an antiarrhythmic agent which acts by increasing the duration of cardiac repolarization is better than those which act by blocking sodium channels.

The above disclosures emphasize the fact that suppression of arrhythmias does not necessarily decrease mortality and that the net effect on mortality is agent specific. In addition, the most important determinant of arrhythmia mortality is the nature and degree of ventricular dysfunction.

All these lead to dramatic changes in the choice of antiarrhythmic drugs for ventricular and supraventricular arrhythmias.

Thus, sotalol emerged as one of the drugs of choice for its beta blocking and antiarrhythmic activities, as it could reduce mortality by preventing ventricular fibrillation in patients with cardiac disease.

Jay W. Mason for the Electrophysiologic Study Versus Electrocardiographic Monitoring (ESVEM) Investigators (New Engl J Med 1993; 329:452–8) has shown that in patients with Ventricular Tachycardia (VT) and Ventricular Fibrillation (VF), sotalol a beta blocker with class III antiarrhythmic activity is better than six other class I antiarrhythmic compounds.

The results of the CAST and ESVEM trials have led to an increased interest in class III antiarrhythmic agents including sotalol (Callaghan et al, Am J. Cardiol, 1996; 78:(4A) (54–60).

Sotalol is being used as a equimolecular mixture of dextro- and laevo-isomer of the molecule. The isomers are equipotent in increasing the duration of repolarization and consequently the action potential duration and believed to be equally effective clinically as antiarrhythmic agent.

However, the laevo-isomer is a more potent beta blocker as compared to the dextro-isomer. As a result racemic sotalol with equal proportion of laevo- and dextro-isomers has more than required beta blocking activity which may compromise the cardiac function particularly in patients with structural heart disease.

In addition to the CAST trial a recent meta analysis of mortality data on 98000 survivors with myocardial infarction also found that class I agents were associated with increased mortality. Only class II and class III drugs were associated with decreased mortality. Unfortunately for a high percentage of these patients at risk, beta blockers are not tolerated or are contraindicated. The Survival With Oral d-Sotalol (SWORD) trial indicated that pure d-sotalol was also not of much benefit in patients with acute myocardial infraction (Am J. Cardiol 1995; 75:1023–1027).

U.S. Pat. No. 5,089,526 describes (+)-sotalol that is the dextro isomer as a class III antiarrhythmic drug capable of lengthening the action potential duration of cardiac cells and thus helpful in treatment of cardiac arrhythmias.

U K Patent 2,286,529 observes that the treatment of cardiac arrhythmias in patients with iscbaemic heart disease especially when accompanied by the signs and symptoms of heart failure presents a difficult problem, since most antiarrhythmic drugs including beta blockers, depress cardiac contractility and may worsen heart failure. In solving this problem this U K Patent finds that a mixture of the isomers of sotalol in which the proportion of l-isomer is significantly less than that of d-isomer will be of use in the treatment of arrhythmias in patients with ischaemic heart disease and/or heart failure. It further discloses a combination of 60 to 99 percentage of d-sotalol with 40 to 1 percentage of racemic or dl-sotalol which corresponds to 80 to 99.50 percentage of d-sotalol with 20 to 0.50 percentage of l-sotalol as the most suitable range for this combination for treatment of heart patients.

SUMMARY OF THE INVENTION

The first objective of the present invention is to provide a safer class III antiarrhythmic drug with controlled beta adrenergic blockade.

The second objective of the present invention is to find out the safest ratio of d- and l-isomer in the combination drug of d- and l-sotalol which satisfies the above criteria.

The present invention provides for a safer antiarrhythmic drug with controlled beta adrenergic activity which comprises a combination of dextro- and laevo-rotatory isomers of sotalol being N-[4-[1-hydroxy-2-[(1-methylethyl) amino] ethyl]phenyl]methane sulfonamide, or their pharmaceutically acceptable salts as active ingredients, wherein the range of ratio of dextro- and laevo-isomer in said combination is from 1.5:1 to 3.5:1.

The invention also provides for pharmaceutical composition with the said combination of dextro- and laevo-isomers of sotalol as active ingredient, particularly oral and parenteral preparations containing such active ingredient.

The invention further provides for a method of treatment of cardiac ailments in mammals including human beings by administration of an optimally effective amount of the said combination of dextro and laevo rotatory isomers of sotalol.

DETAILED DESCRIPTION OF THE INVENTION a. Preparation of Isomeric Mixture of Sotalol

Pure isomers of l-sotalol and d-sotalol were prepared from racemic sotalol as follows.

Racemic sotalol hydrochloride was converted into its base. Chiral separation was carried out by chiral chromatography and the isomers were reconverted back to their hydrochloride form.

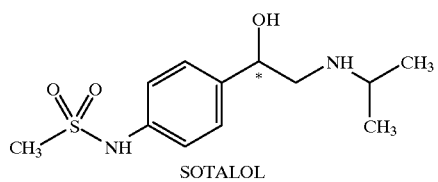

SOTALOL

In addition, using chemical method as described by Le Garrec (1987), enriched d-sotalol hydrochloride and l-sotalol hydrochloride were prepared using mandelic acid and subjected to conversion to the base form, chiral separation and reconversion to hydrochloride salt was carried out. The details of these procedures are given below:

i) Conversion of Sotalol Hydrochloride into Sotalol Base:

In 2 lit. round bottom flask, in 450 ml of water, (±) sotalol hydrochloride (200 g) was added under stirring at room temperature. Under stirring, a solution of 500 g of potassium carbonate in 300 ml of water was added. The stirring was continued for 48 hours. Solid material was separated to give 107 g of (±) sotalol.

ii) Resolution of Racemic Sotalol Base into its Enantiomers:

The solution containing racemic sotalol was chromatographed on a Chiralpak AD column containing 3,5-dimethoxyphenylcarbamoyl derivative. The mobile phase was a 82:18 mixture of n-hexane:absolute ethanol containing 0.2% of diethylamine (AR grade). Based on the method reported in Japanese Patent(JP-1-165569, 1989), the separation was standardised on an analytical Chiralpak AD column and then scaled up on a semipreparative Chiralpak AD column of 2×25 cm dimension. Racemic sotalol base (1.0 g) was dissolved in absolute ethanol (22 ml) by slightly warming to 45–50° C. An aliquot of 2 ml of the solution was injected and eluted with a flow of 7 ml/min. The elution was monitored with a UV detector at 225 nm. On the basis of the chromatographic pattern, various fractions were collected from 23 min to 75 min. All the fractions were analysed with the analytical column to check the optical purity. Pure fractions were combined and evaporated on a rotavapour under reduced pressure at 35–40° C. Colourless solid obtained was collected by filtration with the aid of hexane and tested again for purity by HPLC. In the typical experiment, the optical purity of the fractions collected between 23 min to 35 min was 99.91% and that of those collected between 42 min to 75 min was 99.48%.

iii) Conversion of Sotalol Base into Sotalol Hydrochloride:

d- and l-sotalol bases obtained by the two methods were converted into their hydrochlorides. In a typical experiment, the second eluting component (300 mg) was dissolved in 2-propanol (24 ml) at 30–35° C. during 0.5 h. While stirring, a solution of HCl in propan-2-ol (0.6 ml, 30%) was added and stirred for 1 h at 25° C. The solution was cooled to −2 to 0° C. and then n-hexane (36 ml) was added and stirred for 1 h. Separated crystals were isolated by filtration, washed with hexane (9 ml) and suck dried. The crystals were dried at 30–35° C. under vacuum for 12 h.

| Dry weight | 240 mg |
|---|---|
| Melting point | 202–204° C. |
| Specific rotation | −36.5 (c 15.5, Water) |

After isolating isomers of d- and l-sotalol hydrochloride, various ratios of d and l isomers can be prepared.

b. Determination of Beta Blocking Potency of Different Ratios of Optical Isomers of Sotalol Estimation of the beta blockade of various ratios of d- and l-isomers of sotalol was carried out in the isolated right auricle preparation of rabbit. The spontaneously beating right atrium was dissected and mounted in a 20 ml tissue bath. The resting tension on the atria was set at 1 g. The contractions were recorded using a force displacement transducer. The spontaneous contractions of the right atria were recorded isometrically and the heart rate was obtained as a derived parameter using a ratemeter that gave the output in beats per minute.

Six different ratios of d and l isomers were investigated (1:1, 2:1, 3:1, 4:1, 5:1 and 1:0).

Dose-response-curves (DRC) for isoprenaline in the isolated atria, using the chronotropic response were determined by cumulative addition of isoprenaline. The $pA_2$ values of each of the ratios were estimated using the classical Schild's plot (Schild, 1957) and the values are shown in Table 1

The results showed that the $pA_2$ values of the isomers range from 5.44 for pure d-isomer of sotalol to 6.48 for the dl isomer (1:1). The relationship between the ratios and the $pA_2$ values show good correlations as shown by the analysis of correlations between the ratios and the corresponding $pA_2$ values ($r=-0.97$, $p=0.001$).

TABLE 1

Coniparative pA2 values of isomers of sotalol d/l ratios

| No. | 1:1 | 2:1 | 3:1 | 4:1 | 5:1 | 1:0 |
|---|---|---|---|---|---|---|
| 1 | 6.61 | 6.33 | 6.29 | 5.88 | 5.53 | 5.12 |
| 2 | 6.74 | 6.10 | 5.94 | 5.91 | 6.10 | 5.38 |
| 3 | 6.10 | 6.31 | 5.98 | 6.22 | 6.00 | 5.38 |
| 4 | 6.52 | 6.40 | 6.03 | 5.99 | 5.91 | 5.48 |
| 5 | 6.52 | 6.13 | 6.22 | 5.87 | 5.78 | 5.40 |
| 6 | 6.31 | 6.43 | 6.38 | 6.06 | 5.79 | 5.60 |
| 7 | 6.45 | 6.19 | 6.07 | 6.02 | 5.89 | 5.70 |
| 8 | 6.58 | 6.35 | 6.27 | 6.13 | 5.86 | — |
| 9 | — | — | — | 6.04 | — | — |
| Mean | 6.48 | 6.28 | 6.15 | 6.01 | 5.85 | 5.44 |
| S.D. | 0.20 | 0.12 | 0.16 | 0.12 | 0.17 | 0.19 |

This demonstrated that one could change the beta blocking activity in a ctable way by changing the ratios of the d- and l-isomers of sotalol in a mixture. Now it is to be shown that different ratios of the sotalol isomers have sufficient antiarrhythmic activity in vivo in an appropriate model. For this purpose the ouabain induced arrhythmia model in guinea pig was used. The study was carried out as given below:

c. Demonstration of Antiarrhythmic Activity of Different Ratios of Sotalol Isomers Method: Guinea pigs (Dunken Hartley) of either sex weighing between 400 and 500 g were used for the study.

The animals were anesthetized with urethane (1.25 g/kg. i.p.). The left common carotid artery and left jugular vein were cannulated for arterial blood pressure monitoring and intravenous access respectively. Lead II electrocardiogram, arterial blood pressure, mean arterial blood pressure (MABP), heart rate were monitored throughout the experiment.

By preliminary experiments it was found that the following protocol produced Ventricular tachycardia (VT) and Ventricular fibrillation (VF) in guinea pigs. After initial surgical preparations and allowing 30 minutes for the animal to stabilise the first dose of ouabain (90 µg/kg) was administered over a period of one minute. After the interval of thirty minutes, second dose of ouabain (60 µg/kg) was administered over a period of one minute. One minute after this dose, 0.5 ml saline (in control experiments) was administered over a period of one minute. After an interval of 10 minutes a third dose of ouabain (90 µg/kg) was administered over a period of one minute. Animals were observed for one hour. The test compounds were administered to animals in test group in place of saline to evaluate their antiarrhythmic potential. From the ECG recordings, the incidence of VT, VF and mortality were recorded. The doses of ratios of sotalol isomers studied were 0.1, 0.5 and 2.5 mg/kg. If protection was observed at 0.1 mg/kg dose, a lower dose of 0.02 mg/kg was also tested. When 2.5 mg/kg dose failed to protect adequately, 12.5 mg/kg dose was used.

Interpretation of ECG recordings: Minor disturbance in rhythm was not considered while evaluating ventricular tachyarrhythmias. A run of more than 3 ventricular ectopic beats having wide QRS complexes associated with partial haemodynamic collapse was considered as Ventricular Tachycardia (VT). Total morphological irregularity of repetitive complexes for at least six cycles associated with complete haemodynamic collapse was considered as Ventricular Fibrillation (VF). Successful arrhythmia protection was defined as no occurrence of VT and VF from the injection of saline/test drug till the end of the experiment.

Statistics: Chi square test with continuity correction at 95% confidence limit was applied to find out the statistical significance between control and test groups for incidence of VT, VF and mortality. Whenever, any of the value in a cell was less than 5, Fischer's exact probability test was used.

Results: Different ratios of sotalol in the dose range from 0.02 mg/kg to 12.5 mg/kg were studied in individual groups of animals. The dosage schedule and ratios are given in the Table 2. In all 18 groups were studied and at least 6 animals were used in each group. In control animals ouabain 240 µg/kg in three divided doses induced reproducible ventricular tachyarrhythmias in guinea pigs. It was observed that ventricular arrhythmias appeared after the administration of the third dose. Guinea pigs which responded early i.e. before or within 1 min. of administration of the second dose, were considered early responders and were not included in the study. Animals which did not show ventricular arrhythmias through out the observation period (late responders) in control experiments were included in the study. In the study, control experiments were carried out randomly interspersed in test groups. Among the 42 control animals the incidence of VT was 81%, incidence of VF was 71.4% and the incidence of mortality at 60 minutes was 61.9%.

Protection against VT: dl-sotalol at 0.1, 0.5 and 2.5 mg/kg dose was able to protect against ouabain induced VT. The minimum protective dose of dl-sotalol was 0.1 while complete protection was observed only at 2.5 mg/kg. d-Sotalol was ineffective in protecting against ouabain induced VT.

2:1 ratio (d:l) at the dose of 2.5 mg/kg was able to completely protect against VT. Although a dose of 0.5 mg/kg showed some protection, it was not significant. 2.5:1 ratio (d:l) was also able to completely protect against VT. at the dose 2.5 mg/kg. However, the protection was not complete at a dose of 0.50 mg/kg. 3:1 ratio (d:l) showed protection at 0.5 and 2.5 mg/kg doses, of which, complete protection was observed only at 2.5 mg/kg dose. 4:1 ratio (d:l) showed some protection at 2.5 mg/kg dose but complete protection was observed only at 12.5 mg/kg dose.

Protection against VF: dl-Sotalol exhibited some protection with 0.1 and 0.5 mg/kg doses, but a 2.5 mg/kg dose completely protected the animal from VF.

d-Sotalol was ineffective in protecting against ouabain induced VF.

For both 2:1 ratio (d:l), and 2.5:1 ratio (d:l), the dose of 2.5 mg/kg was completely able to protect against VF. Although a dose of 0.5 mg/kg showed some protection, it was not complete.

4:1 ratio (d:l) was able to protect, completely only at 12.5 mg/kg dose, with some protection at 2.5 mg/kg dose.

TABLE 2

The effect of isomers of sotalol on the incidence of arrhythmia and mortality

| DRUG | DOSE (mg/kg) | N | % INCIDENCE OF VT | % INCIDENCE OF VT | % INCIDENCE OF MORTALITY |
|---|---|---|---|---|---|
| CONTROL | 0.5 ml saline | 42 | 81.0 (34) | 71.4 (30) | 61.9 (26) |
| dl-SOTALOL | 0.02 | 6 | 83.3 (5) | 83.3 (5) | 16.6 (1) |
|  | 0.1 | 6 | 33.3 (2)* | 33.3 (2) | 33.3 (2) |
|  | 0.5 | 6 | 33.3 (2)* | 33.3 (2) | 50.0 (3) |
|  | 2.5 | 10 | 00.0 (0)* | 00.0 (0)* | 60.0 (6) |
| d-SOTALOL | 0.5 | 10 | 70.0 (7) | 70.0 (7) | 50.0 (5) |
|  | 2.5 | 9 | 77.7 (7) | 66.6 (6) | 66.6 (6) |
|  | 12.5 | 6 | 50.0 (3) | 50.0 (3) | 100.0 (6) |
| 2:1 RATIO | 0.5 | 6 | 50.0 (3) | 33.3 (2) | 50.0 (3) |
|  | 2.5 | 6 | 00.0 (0)* | 00.0 (0)* | 16.6 (1) |
| 2.5:1 RATIO | 0.5 | 6 | 33.3 (2)* | 33.3 (2) | 33.3 (2) |
|  | 2.5 | 6 | 0.0 (0)* | 0.0 (0)* | 16.6 (1) |
| 3:1 RATIO | 0.1 | 6 | 66.6 (4) | 66.6 (4) | 33.3 (2) |
|  | 0.5 | 8 | 37.5 (3)* | 25.0 (2) | 37.5 (3) |
|  | 2.5 | 6 | 00.0 (0)* | 00.0 (0)* | 33.3 (2) |
| 4:1 RATIO | 0.5 | 6 | 100.0 (6) | 100.0 (6) | 33.3 (2) |
|  | 2.5 | 6 | 33.3 (2)* | 33.3 (2) | 33.3 (2) |
|  | 12.5 | 6 | 00.0 (0)* | 00.0 (0)* | 66.6 (4) |

*refers to significant difference as compared to corresponding control value (P <0.05)
values in parenthesis show actual incidence.
"N" is number of animals used in each group.

Protection against mortality: dl-sotalol reduced mortality at lower dises. However, there was no protection against mortality at 2.5 mg/kg dose. d-Sotalol exhibits a high mortality rate which increased to 100% at 12.5 mg/kg dose. Both 2:1 and 2.5:1 ratios protected significantly against mortality at 2.5 mg/kg dose and with 2.5:1 ratio the mortality is lower at 0.5 mg/kg dose compared to 2:1 ratio at the same dose. Mortality was low with 0.5 and 2.5 mg/kg dose of 3:1 ratio. Mortality with 4:1 ratio was significantly high at the effective dose of 12.5 mg/kg.

The mortality with the various ratios of isomers of sotalol was analyzed based on the cause of mortality. It was observed that in the control animals $1/3^{rd}$ of the deaths were due to conduction abnormalities and $2/3^{rd}$ mortality was due to tachyarrhythmias. On the other hand with the racemic sotalol at lower doses the deaths were due to tachyarrhythmias and as the dose was increased, the deaths were entirely due to conduction abnormalities. However, with d-sotalol, the deaths were equally due to conduction abnormality as well as tachyarrhythmias at doses 2.5 mg/kg and 12.5 mg/kg. With the 2:1, 2.5:1 and 3:1 d:l ratios of sotalol the mortality was less than that of control groups and the deaths were due to conduction abnormalities. The mortality analysis is given in Table 3.

It could be observed that, at the dose of 2.5 mg/kg, the 2:1 and 2.5:1 ratios completely protects against arrhythmias and the mortality was 16.6%. 3:1 ratio also protected against arrhythmias at 2.5 mg/kg, however the mortality was 33.3%. When the ratio was changed to 4:1, 2.5 mg/kg could not protect against arrhythmias. The VT and VF were 33.3% each. In addition, the mortality rate also was 33.3%. By increasing the dose to 12.5 mg/Kg, 4:1 ratio could protect against arrhythmias but the mortality further increased to 66.6%. In other words 4:1 ratio could protect against arrhythmias only at doses which caused increased mortality.

due to decreased beta blocking activity of 2:1, 2.5:1 and 3:1 ratios as compared to di-sotalol;

(e) protection against VT and VF with 4:1 ratio is only possible at a very high dose of 12.5 mg/kg and accompanied with a very high mortalilty rate of 66.6%.

It may be concluded from the above experimental data that the safe ratio of dextro- and laevo-isomers for administration of the combination drug of d- and l-sotalol is in the range where the ratio of d-isomer in the mixture is higher than a d:l ratio of 1:1 but lower than d:l ratio of 4:1, contrary to the teachings of U.K. Patent 2,286,529 which recommends a d:l ratio of 4:1 or a higher ratio for the d-isomer in the mixture. Thus the safe range of d:l ratio is between 1.5:1 to 3.5:1. Moreover as the mortality rate with same degree of protection against arrhythmia (VT and VF) is showing an increasing trend with d:l ratio 3:1, a safer range of ratio is 1.5:1 to 2.75:1 and a further safer range of ratio with least mortality rate for the same degree of portection against arrhythmia is 2:1 to 2.5:1.

TABLE 3

ANALYSIS OF MORTALITY

| DRUG | DOSE (mg/kg) | N | DEATHS DUE TO CONDUCTION BLOCK (60 MIN) Percentage @ | DEATHS DUE TO TACHY- ARRHYTHMIA (60 MIN) Percentage @ | INCIDENCE OF MORTALITY IN (60 MIN) Percentage @ |
|---|---|---|---|---|---|
| CONTROL | 0.5 ml saline | 42 | 30.8 (8) | 69.2 (18) | 61.9 (26) |
| dl- SOTALOL | 0.02 | 6 | 00.0 (0) | 100.0 (1) | 16.6 (1)* |
|  | 0.1 | 6 | 50.0 (1) | 50.0 (1) | 33.3 (2) |
|  | 0.5 | 6 | 100.0 (3) | 00.0 (0) | 50.0 (3) |
|  | 2.5 | 10 | 100.0 (6) | 00.0 (0)* | 60.0 (6) |
| d- SOTALOL | 0.5 | 10 | 20.0 (1) | 80.0 (4) | 50.0 (5) |
|  | 2.5 | 9 | 50.0 (3) | 50.0 (3) | 66.6 (6) |
|  | 12.5 | 6 | 50.0 (3) | 50.0 (3) | 100.0 (6) |
| 2:1 RATIO | 0.5 | 6 | 100.0 (3) | 00.0 (0) | 50.0 (3) |
|  | 2.5 | 6 | 100.0 (1) | 00.0 (0) | 16.6 (1)* |
| 2.5:1 RATIO | 0.5 | 6 | 100.0 (2) | 00.0 (0) | 33.3 (2) |
|  | 2.5 | 6 | 100.0 (1) | 00.0 (0) | 16.6 (1)* |
| 3:1 RATIO | 0.1 | 6 | 50.0 (1) | 50.0 (1) | 33.3 (2) |
|  | 0.5 | 8 | 100.0 (3) | 00.0 (0)* | 37.5 (3) |
|  | 2.5 | 6 | 100.0 (2) | 00.0 (0) | 33.3 (2) |
| 4:1 RATIO | 0.5 | 6 | 50.0 (1) | 50.0 (1) | 33.3 (2) |
|  | 2.5 | 6 | 100.0 (2) | 00.0 (0) | 33.3 (2) |
|  | 12.5 | 6 | 75.0 (3) | 25.0 (1) | 66.6 (4) |

*refers to significant difference as compared to corresponding control value (P <0.05)
values in parenthesis show actual incidence.
@ percentage deaths out of total mortality.
"N" is number of animals used in each group.

Discussion of the Test Results

The above studies show that:

(a) beta blockade could be safely controlled in a predictable way by changing the ratios of d- and l-isomers of sotalol in a combination containing the mixture of isomers;

(b) the d:l ratios 2:1, 2.5:1 and 3:1 show complete protection against VT and VF at 2.5 mg/kg dose with a lower mortality rate but with the same dose any protection wtih d:l sotalol (ratio 1:1) is accompanied with high mortality rate of 60% contributed solely by conduction block;

(c) 2.5 mg/kg dose of dl-sotalol and 2:1, 2.5:1 and 3:1 ratios of d:l-sotalol completely protected deaths due to tachyarrhythmias;

(d) deaths due to conduction block were increased by dl-sotalol but not by 2:1 and 3:1 ratios which is The combination of the dextro- and laevo-isomers of sotalol according to the invention may be used as such or in the form of their pharmaceutically acceptable salts e.g. hydrochlorides.

The combination can be administered as oral and parenteral preparations and may include pharmaceutically acceptable carriers, diluents and other additives. Optionally one or more pharmacologically active compounds may be included in these preparations.

The combinations and compositions according to the invention are preferably with a ratio of 1.50:1 to 2.75:1 of d:l sotalol and more preferably with a ratio of 2:1 to 2.5:1 of d:l sotalol.

The compositions and combinations according to the invention can be administered either by oral or parenteral route depending on the type of formulation. For preparations intended for oral administration, the active compounds are mixed with suitable additives viz. carriers, stabilizers or inert diluents and converted by the methods known in the art into forms suitable for administration such as tablets, capsule both hard and soft, aqueous, alcoholic or oily suspensions or oily solutions. For oral preparations especially tablet or capsule formulations, an innocuous carrier like gum arabic, magnesium carbonate, potassium phosphate, lactose, glucose, starch, gelatin or dicalcium phosphate can be used. Both dry granulation and wet granulation processes can be used for the production of the granules. Conventional lubricating agents like magnesium stearate, calcium stearate, hydrogenated vegetable oils and/or talc may be used. Antiadherents like colloidal silicon dioxide can also be used.

Alternatively, the active compound may be presented in pure form unassociated with additives in which case a capsule or sachet is the preferred carrier.

For parenteral administration, either subcutaneous or intravenous, the active substances or their pharmaceutically acceptable salts are brought into solution, suspension or emulsion, optionally with conventionally used agents like solubilizers, surfactants, emulsifiers or other similar agents.

The solvents which can be considered for the active combinations and the corresponding pharmaceutically acceptable salts are water, physiological salt solution, alcohols, sugar solutions or a mixture of the various solvents mentioned above. The vehicle employed may be aqueous or non-aqueous or a mixture thereof Non aqueous solvents include lower alcohols, glycols, derivatives of glycols, polyols, oils, derivatives of oils and glycols, such as polyethylene glycols, polyethylene glycol castor oil, propylene glycol, ethyl oleate, or peanut oil may optionally be used.

The salts of the aforementioned active compounds that can be considered are those, depending on the basic nature of those compounds with pharmaceutically acceptable inorganic or organic acids such as hydrochloric acid, hydrobromic acid, sulfuric acid, maleic acid, fumaric acid, succinic acid, tartaric acid and citric acid.

The following non-limiting examples gives the method of preparations of some of these oral and parenteral formulations according to the invention:

EXAMPLE 1

Preparation of a Tablet Formulation of the Sotalol Hydrochloride in the Ratio (+):(−)::3:1

| | | |
|---|---|---|
| i) (±) Sotalol HCl in the ratio (+):(−)::3:1 | 40 mg |
| ii) Starch | 60 mg |
| iii) Microcrystalline Cellulose | 10 mg |
| iv) Crospovidone | 2.5 mg |
| v) Magnesium Stearate | 0.5 mg |
| vi) Talc | 2.0 mg |

EXAMPLE 2

Preparation of an i.v. Product From Sotalol Hydrochloride in the Ratio (+):(−)::3:1

10 ml injection which contains 7.5 mg (+)-Sotalol and 2.5 mg (−)-Sotalol per ml of the injection is prepared as follows:

| | |
|---|---|
| i) (±) Sotalol HCl in the ratio (+):(−)::3:1 | 10.0 mg |

-continued

| | |
|---|---|
| ii) Acetic acid | 60.0 mg |
| iii) Sodium acetate anhydrous | 40.0 mg |
| iv) Sodium chloride | 10.0 mg |
| v) Distilled water | q.s. 10 ml |

The injection so prepared retains the active constituents in the specified ratio for not less than 1 month at 60° C. Furthermore, the ratio is unchanged at 45° C. for 3 months. The solution remains optically clear (Color index<0.002) under these conditions.

What is claimed is:

1. A method of treatment of cardiac ailment in mammals including human beings, which comprises, administering to a mammal in need thereof, an optimally effective amount of a combination of dextro- and laevo-isomers of sotalol or their pharmaceutically acceptable salts wherein the ratio of dextro- and laevo-isomers of sotalol is 1.5:1 to 3.5:1.

2. The method as claimed in claim 1 wherein the ratio of dextro- and laevo-isomers of sotalol is 1.5:1 to 2.75:1.

3. The method as claimed in claim 2 wherein the ratio of dextro- and laevo-isomers of sotalol is 2:1 to 2.5:1.

4. A pharmaceutical composition for use as an antiarrhythmic drug with controlled beta adrenergic blockade which comprises a combination of dextro- and laevorotatory isomers of sotalol or their pharmaceutically acceptable salts as active ingredients wherein the range of ratio of dextro- and laevo-isomers in the said combination is 1.50:1 to 3.5:1.

5. The pharmaceutical composition as claimed in claim 4 wherein the ratio of dextro- and laevo-isomers of sotalol or their pharmaceutically acceptable salts is 1.5:1 to 2.75:1.

6. The pharmaceutical composition as claimed in claim 5 wherein the ratio of dextro- and laevo-isomers of sotalol or their pharmaceutically acceptable salts is 2:1 to 2.5:1.

7. The pharmaceutical composition as claimed in claim 4 wherein the isomers are in the form of their hydrochloride salts.

8. The pharmaceutical composition as claimed in claim 5 wherein the isomers are in the form of their hydrochloride salts.

9. The pharmaceutical composition as claimed in claim 6 wherein the isomers are in the form of their hydrochloride salts.

10. An oral preparation for treatment of cardiac ailment of mammals including human beings which comprises a combination of dextro- and laevo-isomers of sotalol or their pharmaceutically acceptable salts in the ratio as claimed in claim 4 as active ingredients in admixture with pharmaceutically acceptable excepient and additives and optionally one or more other pharmacologically active compounds.

11. An oral preparation for treatment of cardiac ailment of mammals including human beings which comprises a combination of dextro- and laevo-isomers of sotalol or their pharmaceutically acceptable salts in the ratio as claimed in claim 5 as active ingredients in admixture with pharmaceutically acceptable excepient and additives and optionally one or more other pharmacologically active compounds.

12. An oral preparation for treatment of cardiac ailment of mammals including human beings which comprises a combination of dextro- and laevo-isomers of sotalol or their pharmaceutically acceptable salts in the ratio as claimed in claim 6 as active ingredients in admixture with pharmaceutically acceptable excepient and additives and optionally one or more other pharmacologically active compounds.

13. A parenteral preparation for treatment of cardiac ailment of mammals including human beings which comprises a combination of dextro- and laevo-isomers of sotalol or their pharmaceutically acceptable salts in the ratio as claimed in claim 4 as active ingredients in admixture with pharmaceutically acceptable excepient and additives and optionally one or more other pharmacologically active compounds.

14. A parenteral preparation for treatment of cardiac ailment of mammals including human beings which comprises a combination of dextro- and laevo-isomers of sotalol or their pharmaceutically acceptable salts in the ratio as claimed in claim 5 as active ingredients in admixture with pharmaceutically acceptable excepient and additives and optionally one or more other pharmacologically active compounds.

15. A parenteral preparation for treatment of cardiac ailment of mammals including human beings which comprises a combination of dextro- and laevo-isomers of sotalol or their pharmaceutically acceptable salts in the ratio as claimed in claim 6 as active ingredients in admixture with pharmaceutically acceptable excepient and additives and optionally one or more other pharmacologically active compounds.

* * * * *

UNITED STATES PATENT AND TRADEMARK OFFICE
CERTIFICATE OF CORRECTION

PATENT NO. : 6,281,246 B1
DATED : August 28, 2001
INVENTOR(S) : Alangudi Sankaranarayanan It is certified that error appears in the above-identified patent and that said Letters Patent is hereby corrected as shown below:

Column 4,
Line 56, replace "ctable" with -- predictable --.

Column 6,
Table 2, 5th column heading, replace "INCIDENCE OF VT" with -- INCIDENCE OF VF --.
Line 52, replace "dises" with -- doses --.

Column 7,
Line 59, replace "wtih" with -- with --.

Signed and Sealed this

Sixteenth Day of April, 2002

Attest:

Attesting Officer

JAMES E. ROGAN
*Director of the United States Patent and Trademark Office*